(12) United States Patent
Braesch-Andersen

(10) Patent No.: US 8,859,219 B2
(45) Date of Patent: Oct. 14, 2014

(54) PVDF MEMBRANES

(75) Inventor: Sten Braesch-Andersen, Nacka Strand (SE)

(73) Assignee: Mabtech AB, Nacka Strand (SE)

( * ) Notice: Subject to any disclaimer, the term of this patent is extended or adjusted under 35 U.S.C. 154(b) by 0 days.

(21) Appl. No.: 13/308,484

(22) Filed: Nov. 30, 2011

(65) Prior Publication Data

US 2012/0142034 A1 Jun. 7, 2012

Related U.S. Application Data

(63) Continuation of application No. 11/920,033, filed as application No. PCT/EP2006/004356 on May 9, 2006, now abandoned.

(30) Foreign Application Priority Data

May 9, 2005 (GB) .................................. 0509422.2

(51) Int. Cl.

| | |
|---|---|
| G01N 33/00 | (2006.01) |
| B01J 49/00 | (2006.01) |
| B01D 69/02 | (2006.01) |
| B01D 67/00 | (2006.01) |
| G01N 33/543 | (2006.01) |
| B01D 71/34 | (2006.01) |

(52) U.S. Cl.
CPC ............ *B01D 69/02* (2013.01); *B01D 2323/02* (2013.01); *B01D 2325/36* (2013.01); *B01D 67/0088* (2013.01); *G01N 33/54393* (2013.01); *B01D 71/34* (2013.01)
USPC .......................................... 435/7.92; 521/27

(58) Field of Classification Search
USPC .......................................... 435/7.92; 521/27
See application file for complete search history.

(56) References Cited

U.S. PATENT DOCUMENTS

| | | | |
|---|---|---|---|
| 4,340,482 A | 7/1982 | Sternberg | |
| 4,851,121 A | 7/1989 | Yokota et al. | |
| 5,019,260 A * | 5/1991 | Gsell et al. .................... | 210/490 |
| 5,476,590 A | 12/1995 | Brose et al. | |
| 5,827,650 A | 10/1998 | Bronstein et al. | |
| 6,410,252 B1 | 6/2002 | Lehmann et al. | |
| 6,734,386 B1 | 5/2004 | Lauterbach et al. | |
| 7,205,159 B2 | 4/2007 | Cole et al. | |
| 7,662,212 B2 | 2/2010 | Mullette et al. | |
| 8,663,868 B2 * | 3/2014 | Smith et al. .................... | 429/492 |
| 2004/0214180 A1 | 10/2004 | Kobayashi et al. | |
| 2005/0164025 A1 * | 7/2005 | Simonetti et al. ............. | 428/532 |
| 2008/0058224 A1 * | 3/2008 | Lebrun ........................... | 506/26 |
| 2010/0044302 A1 * | 2/2010 | Peters et al. .................. | 210/490 |
| 2010/0297489 A1 * | 11/2010 | Beard ........................... | 429/122 |

FOREIGN PATENT DOCUMENTS

| | | |
|---|---|---|
| DE | 10225501 A1 | 12/2003 |
| EP | 0353460 A2 | 2/1990 |
| EP | 0 419 396 | 3/1991 |
| WO | WO 2001/05492 | 1/2001 |
| WO | WO 2007/057057 A1 | 5/2007 |

OTHER PUBLICATIONS

Chabraoui, F., et al., "Dot-Blot Immunodetection of Antibodies Against $G_{M1}$ and Other Gangliosides on PVDF-P Membranes," *Journal of Immunological Methods*, 165(2):225-230 (1993).

Lin, Y., et al., "Detection of Multiple Cytokines by Protein Arrays from Cell Lysate and Tissue Lysate," *Clin. Chem. Lab. Med.*, 41(2):139-145 (2003).

International Preliminary Report on Patentability dated Nov. 14, 2007, issued in International Application No. PCT/EP2006/004356, with Written Opinion of the International Search Authority attached (8 pages).

International Search Report dated Sep. 4, 2006, issued in International Application No. PCT/EP2006/004356 (3 pages).

* cited by examiner

*Primary Examiner* — Chris L Chin
*Assistant Examiner* — Gary E Hollinden
(74) *Attorney, Agent, or Firm* — Hamilton, Brook, Smith & Reynolds, P.C.

(57) ABSTRACT

The invention provides a method of treating a polyvinyl difluoride (PVDF) membrane comprising:

(a) contacting said membrane with an alcohol and a wetting agent; and (b) drying said membrane.

20 Claims, 5 Drawing Sheets

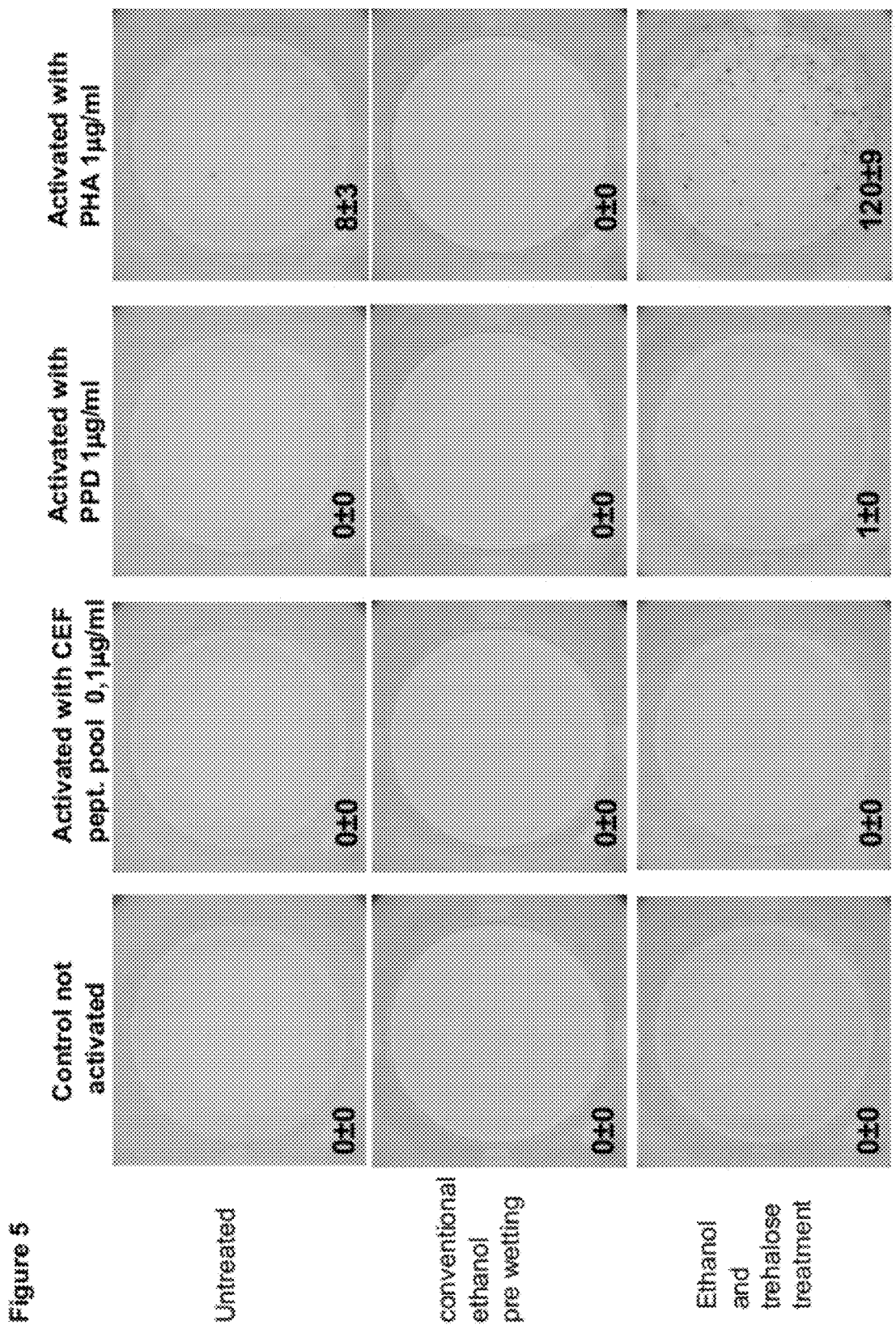

PVDF MEMBRANES

RELATED APPLICATIONS

This application is a continuation of U.S. application Ser. No. 11/920,033, filed Dec. 27, 2007 now abandoned, which is the U.S. National Stage of International Application No. PCT/EP2006/004356, filed on May 9, 2006, published in English, which claims priority under 35 U.S.C. §119 or 365 to United Kingdom Application No. 0509422.2, filed May 9, 2005.

FIELD OF THE INVENTION

The invention relates to a method of treating PVDF membranes to eliminate the need for preactivation. The treated membranes have utility in ELISpot and other assays.

BACKGROUND OF THE INVENTION

Polyvinyl difluoride (PVDF) membranes are commonly used as a solid support in a variety of immunological assays. Due to its high capacity to bind and retain protein, PVDF is an ideal membrane particularly for assays, such as the ELISpot and microarray assays, that are dependent on a high local concentration of the immobilized agent. However, to achieve its high binding properties the PVDF needs to be activated since the membrane in its original form has very hydrophobic properties and comparatively poor binding properties. Activation is normally achieved by treatment with ethanol or methanol which makes the membrane more hydrophilic allowing for aqueous solutions to penetrate into the membrane and thereby increasing the surface area accessible for binding. Typically, the membrane is treated with ethanol for a short period, followed by several rounds of washing before addition of the substance to be coated. It is essential that the membrane is not allowed to dry between the activation and the coating as it then resumes its hydrophobic low-binding properties.

The activation procedure needs to be performed in a strictly defined manner, particularly when the membrane is used for cellular assays, since "overtreatment" (i.e. too much ethanol or too long a treatment duration) has been shown to have a deleterious effect and lead to suboptimal results.

SUMMARY OF THE INVENTION

The present inventors have developed a method of modifying a PVDF membrane in a way that obviates the need for the user to preactivate before coating. Modifying the membrane is this way avoids the risk of "overtreatment". The use of modified membranes also represents a significant simplification in the preparation of assay plates because the coating substance can be added directly to the plate, without the need for prior activation. Accordingly, the present invention provides:

a method of treating a polyvinyl difluoride (PVDF) membrane comprising:
(a) contacting said membrane with an alcohol and a wetting agent; and
(b) drying said membrane;

a PVDF membrane obtainable by a method of the invention;

a method of coating a PVDF membrane of the invention with a protein, said method comprising:
(a) contacting said membrane with a protein;
(b) optionally washing said membrane; and
(c) optionally drying said membrane in the presence of a stabilising agent; and use of a PVDF membrane of the invention in an immunological assay.

BRIEF DESCRIPTION OF THE FIGURES

FIG. 5 shows IL-13 ELISpot results using different coating procedures. (Row 1) untreated plate; (row 2) plate freshly prewetted with ethanol; and (row 3) plates treated with a mixture of ethanol and trehalose and dried. The number of spots in each plate is indicated under each picture (n=4).

DETAILED DESCRIPTION OF THE INVENTION

Figure 1:
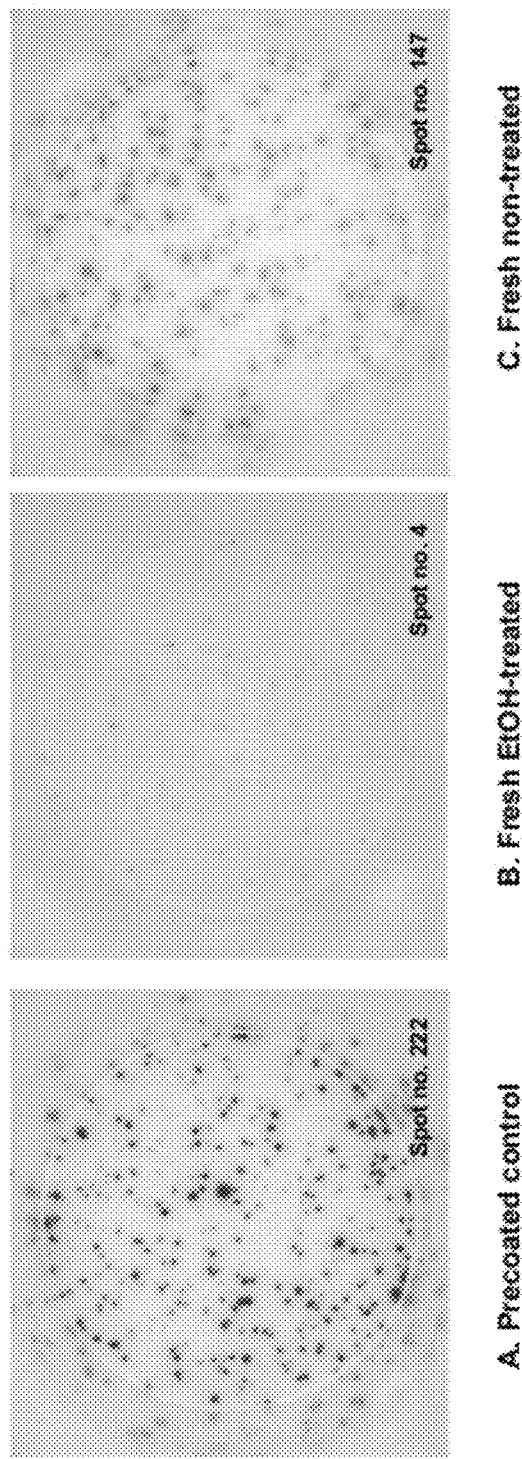
FIG. 1 shows typical IFN-γ ELISpot results using different conventional coating procedures. (A) pretreated control plate; (B) "overtreated" plate; and (c) untreated plate.

The present invention is based on the finding that polyvinyl difluoride (PVDF) membranes can be "activated" in a permanent way if they, after or during activation with ethanol, are saturated with substances ("wetting agents") that make the membrane more hydrophilic. This way the membrane can be dried and stored long-term while still retaining its high binding properties. The method of the invention may also be applied to other hydrophobic membranes suitable for use in the ELISpot assay.

The invention provides a method of treating, or activating, a PVDF membrane comprising:
(a) contacting said membrane with an alcohol and a wetting agent; and
(b) drying said membrane.

Step (a) may comprise contacting said membrane with a mixture of the alcohol and the wetting agent. Alternatively, the membrane may be first contacted with alcohol and then with the wetting agent. The membrane may be washed to remove the alcohol prior to adding the wetting agent.

Any suitable alcohol may be used in step (a). The alcohol is preferably methanol or ethanol but other alcohols such as propanol or isopropanol may be used.

The wetting agent is any substance that makes the PVDF membrane more hydrophilic. The wetting agent is a hydrophilic or partly hydrophilic compound, i.e. a compound which is both hydrophilic and hydrophobic. The wetting agent is preferably non-toxic. The wetting agent typically has no effect on cell activation or cell behaviour. The wetting agent is generally endotoxin free. Suitable wetting agents include phosphate buffered saline (PBS), carbonate salts, carbohydrates, proteins and amino acids.

In one embodiment, two or more, such as 3, 4, 5 or 6, different wetting agents may be used in combination. For example, two or more different carbohydrates, such as two or more of the sugars described herein, two or more different carbonate salts, two or more different proteins or two or more different amino acids may be used as wetting agents. Alternatively, two or more different types of wetting agent may be used in combination. For example, a carbohydrate and a protein, amino acid and/or carbonate salt may be used, optionally in PBS, a protein, amino acid and/or carbonate salt may be used, optionally in PBS or an amino acid and a carbonate salt may be used, optionally in PBS.

The carbohydrate is typically a sugar. Examples of suitable sugars include lactose, glucose, sucrose, fructose, mannose, inositol, glucosamine, arabinose, xylose and trehalose. The protein may be any protein that does not bind to substances, such as cytokines, that the membrane may subsequently be used to detect.

The protein may, for example, be an antibody which does not interact with any of the molecules of interest in the assay for which the membrane is intended. Suitable proteins are typically from 5 to 5000 amino acids in length. The protein is typically in purified form. The protein is generally one which is stable over time to allow long term storage of the plates.

Any amino acid or a mixture of any two or more amino acids may be used as the wetting agent. The amino acid may be alanine, arginine, asparagine, aspartate, cysteine, glutamine, glutamate, glycine, histidine, isoleucine, leucine, lysine, methionine, phenylalanine, proline, serine, threonine, tryptophan, tyrosine or valine or any combination thereof. Glycine is a preferred amino acid.

The time for which the membrane is contacted with the alcohol and wetting agent is not critical. The membrane is typically contacted with a mixture of alcohol and the wetting agent for from about 30 seconds to about 10 minutes. In practical terms, the membrane may be subjected to drying immediately after the mixture of alcohol and wetting agent is added to the membrane. Alternatively, the membrane is typically contacted with alcohol for from about 30 seconds to about 10 minutes followed by contacting the membrane with the wetting agent for from about 30 seconds to about 10 minutes. The wetting agent may be added immediately after the alcohol. The membrane may be subjected to drying immediately after the wetting agent is added.

Generally, 70% alcohol, for example 70% ethanol or 70% methanol is used in a method of the invention. The alcohol may also be used at other concentrations, for example from 30% to 90%.

Suitable concentrations of the different wetting agents are as follows. Carbohydrates may be used at a concentration of from about 0.05% to about 5%, for example from about 0.1% to about 4% or about 0.2% to about 3%. The carbohydrate may be present in PBS. Glycerol may be used at a concentration of from about 0.1% to about 10%, for example at about 1%, 2% or 5%.

PBS may be used at various different dilutions, such as from about 0.5 to about 10 times the normal dilution, such as at the normal dilution or twice the normal dilution. The normal dilution of PBS is 20 mM phosphate and 50 mM NaCl.

An amino acid, or combination of amino acids, may be used at a concentration of from 0.05% to 5%, for example at 0.5%, 1% or 2%.

A protein, such as an antibody may be used at a concentration of from about 0.1 $\mu ml^{-1}$ to about 10 $\mu ml^{-1}$, such as at about 1 $\mu gml^{-1}$, 2 $\mu ml^{-1}$ or 5 $\mu ml^{-1}$.

The membrane is typically dried in the presence of the wetting agent, and optionally the alcohol, under sterile conditions. For example, the membrane may be dried in a dry climate room under a sterile flow. Sterile conditions may be applied by keeping the plates under a UV light. Alternatively, drying may be carried out under non-sterile conditions and the plates may be sterilized by irradiation after drying. Drying may also be carried out under a vacuum. The plates may be heated to aid the drying process. The drying time is not critical and depends on the volume of ethanol/wetting agent added and the drying conditions.

The drying step is typically carried out in the absence of a stabilising agent, particularly in the case where the wetting agent is a protein.

The PVDF membrane may be in any format. For example, a sheet of PVDF may be treated by a method of the invention. Alternatively, the PVDF membrane may be in a format suitable for a particular assay. For example, the PVDF membrane may be in a 96 well ELISpot plate. In a 96 well ELISpot plate the PVDF may be in every well, a strip of wells or a single well.

The present invention also provides a method of treating a PVDF membrane which further comprises:
(a) contacting the dried membrane with a protein;
(b) optionally washing said membrane; and
(c) optionally drying said membrane in the presence of a stabilising agent.

The protein may be any protein that is capable of specifically binding to a substance to be detected in an assay. The protein may, for example, be an antibody or fragment thereof.

The antibody may be any antibody or binding protein that is useful in an immunoassay. For example, the antibody may be one specific for a cytokine such as IFN-γ, IL-10, IL-12 or IL-13.

The invention also provides a PVDF membrane obtainable by a method of the invention. The PVDF membrane is typically provided in a dried form. The membrane of the invention does not require activation prior to its subsequent use, i.e. coating of the membrane with a binding protein. The membrane of the invention may be coated by contacting it directly with an antibody or other binding protein in solution.

Accordingly, the invention also provides a method of coating a PVDF membrane of the invention with a protein, said method comprising:
(a) contacting said membrane with a protein;
(b) optionally washing said membrane; and
(c) optionally drying said membrane in the presence of a stabilising agent.

It is not essential that the PVDF membrane is dried. After contacting the membrane with a protein, the membrane may be used straightaway in an assay.

The present invention provides the use of a PVDF membrane according to the invention in an immunological assay. Examples of immunological assays include ELISpot and ELISA assays.

The PVDF membranes of the invention may be provided together with instructions for coating the membrane with a protein, such as an antibody, and/or instructions for carrying out an immunological assay. The membranes may also be provided together with any components of an immunological assay, such as an antibody. Thus, the invention also provides an immunoassay kit comprising a membrane of the invention together with one or more of an antibody, a buffer, a cell culture medium, an enzyme-conjugated antibody, a streptavidin-enzyme conjugate, an enzyme substrate and/or assay instructions. The antibody may be for binding to the membrane as a capture antibody or may be an antibody for detecting a captured reagent. The detection antibody may be biotinylated. Where the kit comprises a biotinylated detection antibody it typically also comprises a streptavidin-enzyme conjugate.

The following Examples illustrate the invention.

EXAMPLES

Comparative Example 1

To demonstrate the effect of treating and overtreating a PVDF ELISpot plate with ethanol, IFN-γ ELISpot assays were carried out using different conventional coating procedures.

Commercially available precoated ELISpot plates (Mabtech, Stockholm, Sweden) were used as a precoated control plate. In these plates, the IFN-γ antibodies have been coated onto ethanol activated membranes followed by drying in the presence of stabilising agents. This procedure has previously been shown to produce plates that are optionally sensitive and highly stable when stored long term under various conditions. Also, although the membrane is activated by ethanol, the treatment conditions are chosen such that the negative effects of ethanol treatment are not observed.

To demonstrate the effects of overtreatment, a PVDF ELISpot plate was prewetted with 100 µl 70% ethanol/well for 2 minutes prior to coating with anti-IFN-γ antibody (1D1K) at 1.5 µg per well An untreated plate coated with anti-IFN-γ antibody (1D1K) at 1.5 µg per well was also used in this Example.

The ELISpot plates were incubated with $10 \times 10^4$ peripheral blood mononuclear cells (PBMC)/well overnight in the presence of antigenic peptides (CEF peptide pool). The cells were removed and a secondary enzyme-conjugated antibody (7-B6-1) against IFN-γ was added followed by development with streptavidin-alkaline phosphatase conjugate (SA-ALP) and subsequently with substrate (BC1P/NBT). Spots were counted using an automated ELISpot reader from AID, Germany.

FIG. 1 shows typical results from an ELISpot with a correctly activated well (A) and an "overtreated" well (B). As can be seen, overtreatment leads to significantly reduced number of spots which are also less distinct and thereby more difficult to evaluate. The effect can vary substantially between different wells within a plate and thereby result in poor reproducibility and generally unreliable results. To avoid the problem of overtreatment, some ELISpot users choose to coat the membrane without prior activation. This generally gives a better reproducibility but a diminished sensitivity and poor spot quality (C).

To control the adverse effect of the ethanol treatment, the protocol currently supplied by the current leading manufacturer of ELISpot plates, Millipore requires a very short treatment (<1 min) with a small volume of ethanol or methanol (15 µl/well in a 96 well plate). However, these conditions are not always easy to follow in practice and may not be sufficient to avoid the negative effect.

Example 1

Treatment of PVDF Membranes with Ethanol and a Wetting Agent Using 2-Step and 1-Step Procedures In the following experiments, 96 well ELISpot plates were treated with ethanol and a wetting agent by either a 2-step or a 1-step procedure.

In the 2-step procedure, the plates were activated in a conventional way with 70% ethanol (50 µl/well for 2 min) followed by washing with distilled water. 25-50 µl/well wetting agent was thereafter added and the plates were dried under sterile conditions.

In the 1-step procedure, the plates were subjected to a mixture of ethanol and wetting agent (0.2% trehalose). 50 µl or more of this mixture was added into each well followed by drying under sterile conditions.

Several different compounds were tested to achieve the desired wetting effect. These included salts such as PBS (phosphate buffered saline) and carbonate salts, sugars such as lactose, glucose and trehalose as well as proteins, glycerol and the amino acid glycine.

After drying, the plates were packed with dry-packs and kept at room temperature until used.

The plates used as a comparison in the experiments, were commercially available precoated ELISpot plates (Mabtech, Stockholm Sweden) here referred to as precoated control.

IFN-γ ELISpot arrays were performed on the variously treated plates as follows.

In the IFN-γ test ELISpot assays, the 2-step procedure was carried out using 2% glycerol (FIG. 2B) or 2 µg of an irrelevant antibody (FIG. 2C) and the 1-step procedure was carried out using a mixture of 50 µl 70% ethanol and 0.2% trehalose.

Figure 2:
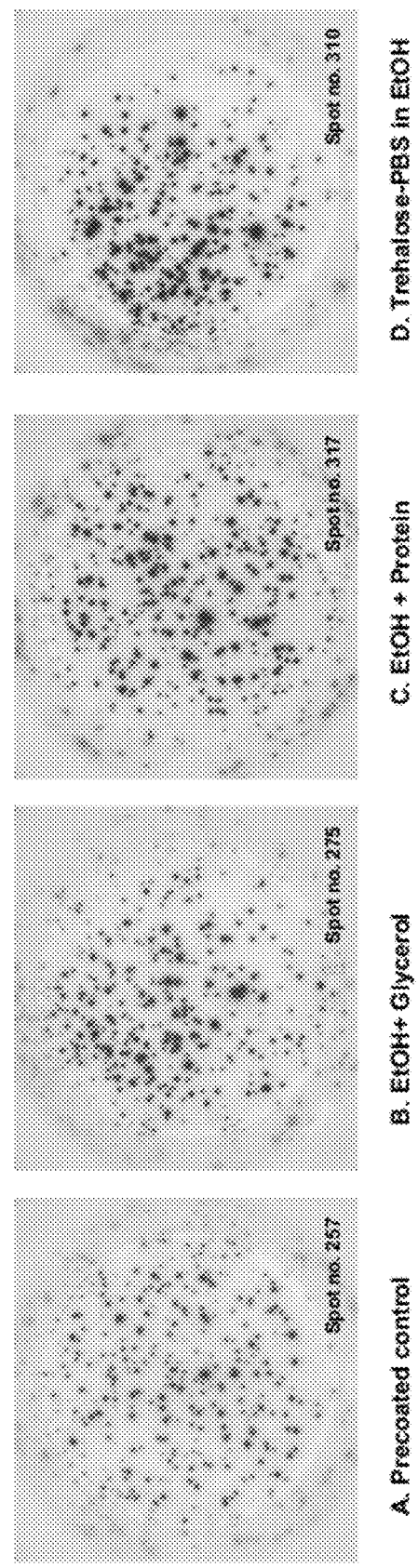
FIG. 2 shows typical IFN-γ ELISpot results using different coating procedures. (A) precoated control plates; (B) plates wetted with ethanol and dried with glycerol; (C) plates wetted with ethanol and dried with protein (2 μg irrelevant antibody); and (D) plates treated with a mixture of ethanol and trehalose and dried. In control wells without antigen the number of spots was always less than 5.

In the test IFN-γ ELISpot assays, PBMC ($10 \times 10^4$/well) were incubated with IFN-γ-coated plates in the presence of stimulating antigenic peptides (CEF peptide pool). After incubation the cells were removed and the plates developed and analysed as described above. Typical results are shown in FIG. 2.

As exemplified in FIG. 2B and FIG. 2C, several of the coating protocols using the 2-step procedure produced results that were comparable to the precoated control (FIG. 2A) both in relation to the number and quality of spots. For instance, glycerol gave distinct spots (FIG. 2B) and similarly protein in the form of an irrelevant antibody served as a good wetting agent (FIG. 2C).

Good results were also obtained with the 1-step procedure, where the wetting agent was added together with the 70% ethanol. Plates treated with a mixture of ethanol and trehalose in PBS (FIG. 2D) gave results very similar to those seen using both the precoated plate (FIG. 2A) and the plates where the ethanol and prewetting agent had been added sequentially (FIG. 2B). Due to its good performance and simpler procedure the 1-step protocol was further evaluated in a number of experiments and with a variety of cytokines.

Example 2

IL-10, IL-12 and IL-13 ELISpot Assays Using PVDF Membranes Treated Using a 1-Step Procedure IL-10, IL-12 and IL-13 ELISpot test assays were carried out using untreated plates (no prewetting prior antibody coating), plates treated with ethanol by a conventional method (freshly prewetted with 100 µl 70% ethanol/well for 2 minutes prior to coating with antibody) and plates treated with a mixture of ethanol and trehalose according to the 1-step procedure described in Example 1 prior to coating with 15 µml$^{-1}$ of the monoclonal antibodies anti-IL-10 (9D7), anti-IL-12 (IL-12-1) and anti-IL-13 (IL-13-1), respectively.

In the IL-10, IL-12 and IL-13 assays, PBMC ($125 \times 10^3$/well) were cultured overnight in the plates without stimulation or with stimulation by 0.1 µg/ml CEF peptide pool for specific stimulation, 1 µg/ml PPD (purified protein derivative) for specific stimulation or 1 μg/ml PHA (phytohemagglutinin) for polyclonal activation. After overnight incubation, the cells were removed and the plates developed with biotinylated secondary antibodies (12G8-biotin, IL-12-II-biotin or IL-13-II biotin) followed by SA-ALP. ALP substrate (BCIP/NBT) was on for 10 minutes. The plates were analysed as described above.

Figure 3:
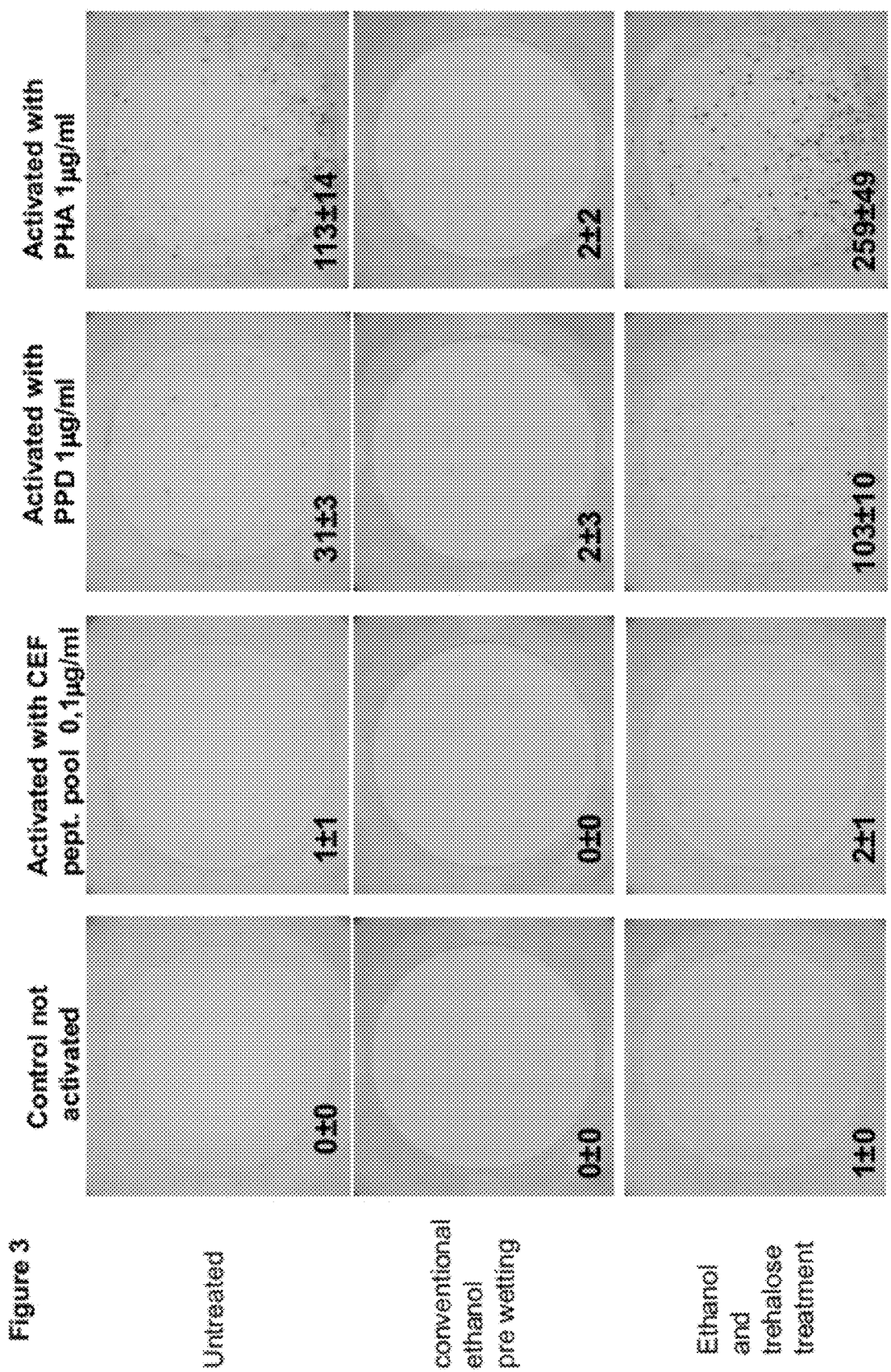
FIG. 3 shows typical IL-10 ELISpot results using different coating procedures. (Row 1) untreated plate; (row 2) plate freshly prewetted with ethanol; and (row 3) plates treated with a mixture of ethanol and trehalose and dried. The number of spots in control well without antigen was below 5 in each plate. The number of spots in each plate is indicated under each picture (n=4).
Figure 4:
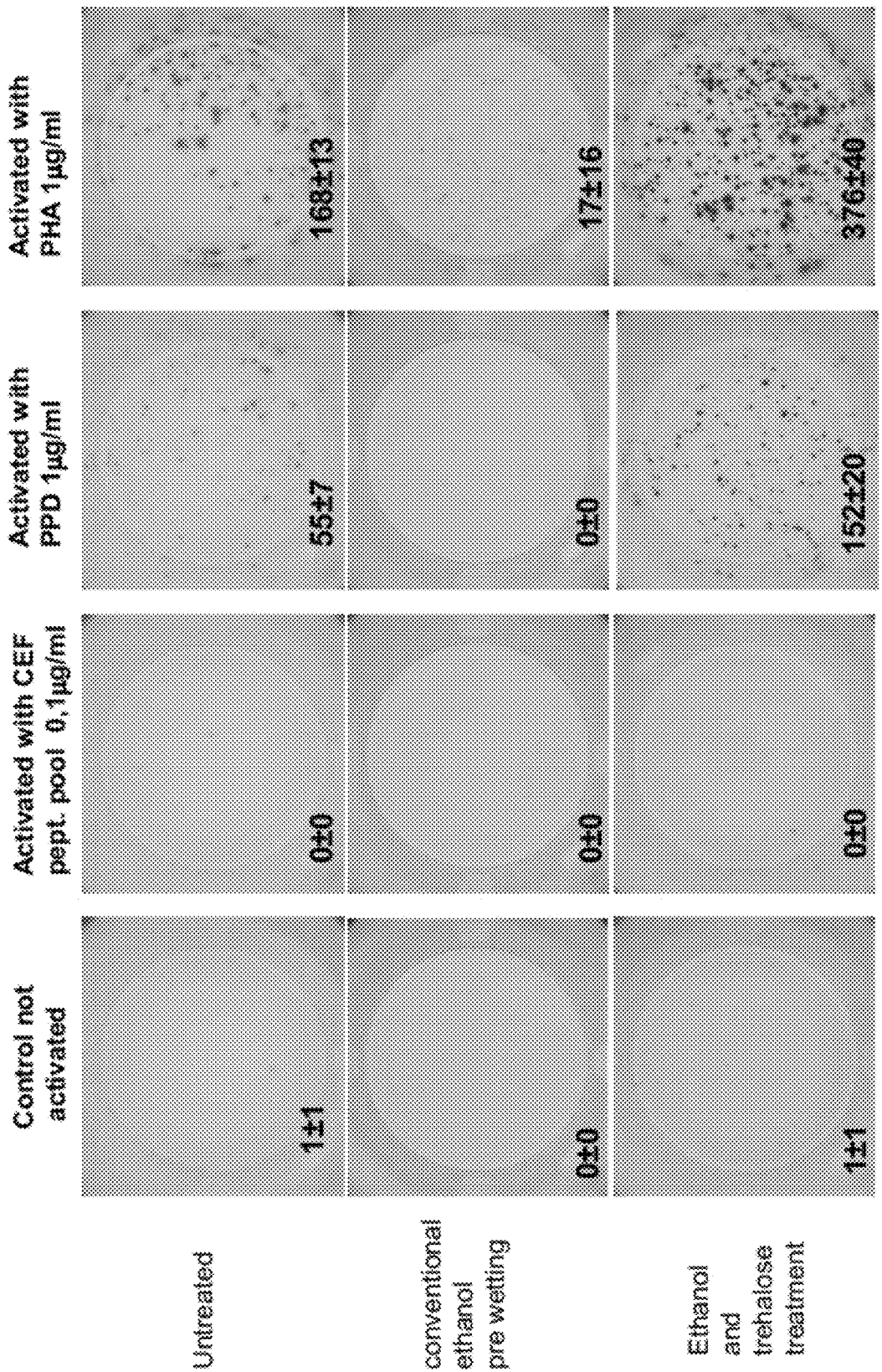
FIG. 4 shows IL-12 ELISpot results using different coating procedures. (Row 1) untreated plate; (row 2) plate freshly prewetted with ethanol; and (row 3) plates treated with a mixture of ethanol and trehalose and dried. The number of spots in control wells without antigen was below 5 in all plates. The number of spots in each plate is indicated under each picture (n=4).

The results of the IL-10 assays are shown in FIG. 3, the results of the IL-12 assays are shown in FIG. 4 and the results of the IL-13 assays in FIG. 5.

As seen in FIGS. 3 and 4, good results were obtained when analysing IL-10 and IL-12 production in the ELISpot after various types of activation. As before, overtreatment of plates with ethanol resulted in consistently poor results (middle row) and similarly coating without previous activation gave suboptimal spot numbers and more diffuse spots (top row).

This was even more apparent with the cytokine IL-13 which has slower kinetics requiring two days of stimulation and cell cultivation (rather than 1 day as for many other cytokines) to achieve optimal results. Although suboptimal with regards to both spot numbers and spot intensity, a clear (IL-13) response could be detected in PHA-stimulated cultures also after overnight incubation when using the method-treated plates (FIG. 5, row 3). However, these spots were not or were only barely detectable in the other two plates (FIG. 5, rows 1 and 2).

Example 3

Antibody Uptake on Treated Surfaces

To demonstrate the change in protein adsorbing capacity between non-treated plates, plates treated with the described method and plates freshly activated with ethanol, were coated with the monoclonal antibody 1D1K at a concentration of 15 μg/ml for 3 hours at room temperature. As shown in Table 1, binding was highest in wells coated according to the conventional procedure, indicating that the poor ELISpot results obtained in these wells (FIG. 1B) are not due to an insufficient amount of coated antibody. Wells treated according to the described method bound similar or slightly lower amounts of antibody as when using conventional coating whereas the binding to a non-activated membrane was substantially lower.

TABLE 1

Binding of antibody to PVDF membranes with and without prior activation.

| | |
|---|---|
| Bound to ethanol-wetted plates: | 31.3% |
| Bound to non-treated plates: | 11.1% |
| Bound to method treated plates: | 26.3% |

The amount of bound antibody was indirectly measured by analysing the concentration of non-bound antibody in ELISA. The percentage bound is estimated by comparing with the original antibody solution.

What is claimed is:

1. A method of activating a polyvinyl difluoride (PVDF) membrane for use in an immunological assay comprising:
   (a) contacting an untreated polyvinyl difluoride membrane with an alcohol, washing said membrane, and contacting said membrane with a wetting agent, wherein said membrane is saturated with the wetting agent; and
   (b) drying said membrane in the presence of the wetting agent, wherein said wetting agent is selected from the group consisting of phosphate buffered saline, a carbonate salt, and a carbohydrate.

2. The method of claim 1, wherein the alcohol is selected from ethanol and methanol.

3. The method of claim 1, wherein the carbohydrate is lactose, sucrose, glucose, trehalose, fructose, mannose, inositol, glucosamine, arabinose or xylose.

4. The method of claim 1, wherein the carbohydrate is a sugar.

5. The method of claim 1, wherein said method further comprises:
   (c) contacting said membrane with a protein;
   (d) optionally washing said membrane; and
   (e) optionally drying said membrane in the presence of a stabilising agent.

6. The method of claim 5, wherein the protein is an antibody.

7. The method of claim 6, wherein the antibody is an antibody to a cytokine.

8. The method of claim 5, wherein the method further comprises (f) carrying out an immunological assay.

9. The method of claim 8, wherein the immunological assay is an ELISA or ELISpot assay.

10. A method of activating a polyvinyl difluoride (PVDF) membrane for use in an immunological assay comprising:
    (a) contacting an untreated polyvinyl difluoride membrane with an alcohol and a wetting agent, wherein said membrane is saturated with the wetting agent; and
    (b) drying said membrane in the presence of the wetting agent, wherein said wetting agent is a sugar.

11. The method of claim 10, wherein step (a) comprises contacting said membrane with a mixture of the alcohol and the wetting agent.

12. The method of claim 10, wherein step (a) comprises:
    (i) contacting said membrane with the alcohol;
    (ii) washing said membrane; and
    (iii) contacting said membrane with the wetting agent.

13. The method of claim 10, wherein the alcohol is selected from ethanol and methanol.

14. The method of claim 10, wherein the sugar is lactose, sucrose, glucose, trehalose, fructose, mannose, inositol, glucosamine, arabinose or xylose.

15. The method of claim 10, wherein said method further comprises:
    (c) contacting said membrane with a protein;
    (d) optionally washing said membrane; and
    (e) optionally drying said membrane in the presence of a stabilising agent.

16. The method of clam 15, wherein the protein is an antibody.

17. The method of claim 16, wherein the antibody is an antibody to a cytokine

18. The method of claim 15, wherein the method further comprises (f) carrying out an immunological assay.

19. The method of claim 18, wherein the immunological assay is an ELISA or ELISpot assay.

20. A method of coating a polyvinyl difluoride (PVDF) membrane, comprising:
    (a) obtaining a PVDF membrane made by a method comprising:
        (i) contacting an untreated polyvinyl difluoride membrane with an alcohol and a wetting agent, wherein said membrane is saturated with the wetting agent; and
        (ii) drying said membrane in the presence of the wetting agent, wherein said wetting agent is a sugar;
    (b) contacting said membrane of step (a) with a protein;
    (c) optionally washing said membrane; and
    (d) optionally drying said membrane in the presence of a stabilising agent.

* * * * *